(12) United States Patent
Khachik

(10) Patent No.: US 7,173,145 B2
(45) Date of Patent: *Feb. 6, 2007

(54) PROCESS FOR EXTRACTION AND PURIFICATION OF LUTEIN, ZEAXANTHIN AND RARE CAROTENOIDS FROM MARIGOLD FLOWERS AND PLANTS

(75) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/497,077

(22) PCT Filed: Jan. 17, 2002

(86) PCT No.: PCT/US02/01108

§ 371 (c)(1),
(2), (4) Date: Oct. 4, 2004

(87) PCT Pub. No.: WO03/048284

PCT Pub. Date: Jun. 12, 2003

(65) Prior Publication Data

US 2005/0038271 A1    Feb. 17, 2005

Related U.S. Application Data

(60) Provisional application No. 60/333,747, filed on Nov. 29, 2001.

(51) Int. Cl.
*C07C 1/00* (2006.01)
(52) U.S. Cl. .................... 554/20; 554/13; 554/14; 554/19; 560/534
(58) Field of Classification Search ................ 554/13, 554/14, 19, 20; 560/534
See application file for complete search history.

(56) References Cited

U.S. PATENT DOCUMENTS

| | | | |
|---|---|---|---|
| 4,048,203 | A | 9/1977 | Philip |
| 5,382,714 | A | 1/1995 | Khachik |
| 5,523,494 | A | 6/1996 | Torres-Cardona et al. |
| 5,648,564 | A | 7/1997 | Ausich et al. |
| 5,780,693 | A | 7/1998 | Bernhard et al. |
| 5,876,782 | A | 3/1999 | Sas et al. |
| 5,902,890 | A | 5/1999 | Nitsche et al. |
| 5,973,211 | A | 10/1999 | Rodriguez |
| 5,998,678 | A | 12/1999 | Sanroma Virgili et al. |
| 6,191,293 | B1 * | 2/2001 | Levy ............... 554/12 |
| 6,262,284 | B1 * | 7/2001 | Khachik ............ 554/14 |
| 2003/0158455 | A1 | 8/2003 | Khachik |

FOREIGN PATENT DOCUMENTS

| | | |
|---|---|---|
| EP | 0 242 148 B1 | 1/1993 |
| EP | 0 349 138 B1 | 8/1994 |
| GB | 1 515 238 | 6/1978 |
| GB | 2 160 874 A | 1/1986 |
| GB | 2 218 989 A | 11/1989 |
| JP | 61-109764 | 5/1986 |
| JP | 07-304978 | 11/1995 |
| WO | WO 98/03480 A1 | 1/1998 |
| WO | WO 99/20587 A1 | 4/1999 |
| WO | WO 02/04415 A2 | 1/2002 |
| WO | WO 03/048284 A1 | 6/2003 |

OTHER PUBLICATIONS

Auweter, H., et al., "Supramolecular Structure of Precipitated Nanosize β-Carotene Particles," *Angew. Chem. Int. Ed.* 38:2188-2191, Wiley-VCH Verlag GmbH (1999).

Bone, R.A., et al., "Preliminary Identification of the Human Macular Pigment," *Vision Res.* 25:1531-1535, Pergamon Press Ltd. (1985).

Bone, R.A., et al., "Stereochemistry of the Human Macular Carotenoids," *Invest. Ophthalmol. Vis. Sci.* 34:2033-2040, Lippincott-Raven Publishers (1993).

Khachik, F., et al., "Identification of Lutein and Zeaxanthin Oxidation Products in Human and Monkey Retinas," *Invest. Ophthalmol. Vis. Sci.* 38:1802-1811, Lippincott-Raven Publishers (1997).

Khachik, F., et al., "Identification, Quantification, and Relative Concentrations of Carotenoids and Their Metabolites in Human Milk and Serum," *Anal. Chem.* 69:1873-1881, American Chemical Society (1997).

Khachik, F., et al., "Lutein, Lycopene, and Their Oxidative Metabolites in Chemoprevention of Cancer," *J. Cellular Biochem., Suppl.* 22:236-246, Wiley-Liss, Inc. (1995).

Khachik, F., et al., "Separation and Identification of Carotenoids and Their Oxidation Products in the Extracts of Human Plasma," *Anal. Chem.* 64:2111-2122, American Chemical Society (1992).

Khachik, F., et al., "Separation, Identification, and Quantification of Carotenoids in Fruits, Vegetables, and Human Plasma by High Performance Liquid Chromatography," *Pure & Appl. Chem.* 63:71-80, IUPAC (1991).

(Continued)

*Primary Examiner*—Deborah D. Carr
(74) *Attorney, Agent, or Firm*—Sterne, Kessler, Goldstein & Fox P.L.L.C.

(57) ABSTRACT

A process for extracting and isolating carotenoid esters or carotenoids in high purity from plants without the use of harmful organic solvents. Zeaxanthin esters were isolated and purified from the berries of Lycium Chinese Mill (LCM berries). The esters isolated according to the invention contain substantially no isomerized double bonds. The purified carotenoid esters or carotenoids isolated by this process are free from impurities and serve as a safe source of nutritional supplement for human consumption as well as providing a suitable and effective color additive for human foods.

38 Claims, No Drawings

OTHER PUBLICATIONS

Khachik, F. and Beecher, G.R., "Separation of Carotenol Fatty Acid Esters by High-Performance Liquid Chromatography," *J. of Chromatography*, 449:119-133, Elsevier Science Publishers B.V. (1988).

Lenfant, C. and Thyrion, F.C., "Extraction of carotenoids from palm oil II. Isolation methods," *Oléagineux Corps gras Lipides* 3:294-307, John Libbey Eurotext (1996).

Murakoshi, M., et al., "Potent Preventive Action of α-Carotene against Carcinogenesis: Spontaneous Liver Carcinogenesis and Promoting Stage of Lung and Skin Carcinogenesis in Mice Are Suppressed More Effectively by α-Carotene Than by β-Carotene," *Cancer Res.* 52:6583-6587, American Association for Cancer Research (1992).

Seddon, J.M., et al., "Dietary Carotenoids, Vitamins A, C, and E, and Advanced Age-Related Macular Degeneration," *J. Am. Med. Assoc.* 272:1413-1420, American Medical Association (1994).

*The Chemist's Companion: A Handbook of Practical Data, Techniques, and References,* Gordon, A.J. and Ford, R.A., eds., John Wiley & Sons, Inc., New York, NY, pp. 451-452 (1972).

Tyczkowski, J.K. and Hamilton, P.B., "Research Note: Preparation of Purified Lutein and Its Diesters from Extracts of Marigold (*Tagetes erecta*)," *Poultry Sci.* 70:651-654, Poultry Science Association, Inc. (1991).

Patent Abstracts of Japan, Publication No. 61-109764, English Language Abstract for JP Patent Application No. 59-229023 (Document AN1).

Patent Abstracts of Japan, Publication No. 07-304978, English Language Abstract for JP Patent Application No. 06-098955 (Document AM2).

International Search Report for International Application No. PCT/US02/01108, US Commissioner of Patents and Trademarks, Washington, DC, mailed on Jul. 11, 2002.

* cited by examiner

PROCESS FOR EXTRACTION AND PURIFICATION OF LUTEIN, ZEAXANTHIN AND RARE CAROTENOIDS FROM MARIGOLD FLOWERS AND PLANTS

BACKGROUND OF THE INVENTION

1. Field of the Invention

The invention is in the field of natural products chemistry. In particular, disclosed is a process for the isolation of lutein and zeaxanthin diesters with substantially no isomerized by-products, and a simultaneous process for extraction, isolation, and purification of lutein, zeaxanthin, and several rare carotenoids from Marigold flowers, Lycium Chinese Mill, and green plants.

2. Background Art

Carotenoids are amongst the most widespread of the naturally occurring groups of pigments and are found in all families of the plant and animal kingdoms. To date, as many as seven hundred carotenoids have been isolated from various sources and their chemical structures have been characterized. Numerous epidemiological studies in various populations have shown that consumption of substantial amounts of fruits and vegetables rich in carotenoids reduces the risk of acquiring several types of cancers. As a result, for nearly two decades, scientists have been focusing most of their attention on investigating the protective effect of beta-carotene in prevention of cancer, cardiovascular and eye diseases. This is despite the fact that beta-carotene is only one of the prominent carotenoids found in fruits and vegetables whose consumption has been associated with health benefits in humans. The reasons for such an intense focus can be attributed to the pro-vitamin A activity of beta-carotene and the lack of commercial availability of other prominent food carotenoids.

During the past decade, carotenoids have been isolated, identified, and quantified from fruits and vegetables commonly consumed in the U.S. These studies have revealed that as many as 40 to 50 carotenoids may be available from the diet and absorbed, metabolized, or utilized by the human body (Khachik et al., *Pure Appl. Chem.* 63:71–80 (1991)). However, among these, only 13 carotenoids and 12 of their stereoisomers are routinely found in human serum and milk (Khachik et al., *Anal. Chem.* 69:1873–1881 (1997)). In addition, there are 8 carotenoid metabolites and one stereoisomer in human serum or plasma which result from a series of oxidation-reduction reactions of three dietary carotenoids, namely, lutein, zeaxanthin, and lycopene. These metabolites were first isolated and characterized by Khachik et al., *Anal. Chem.* 64:2111–2122 (1992)). In another study, the ingestion of purified supplements of dietary (3R,3'R,6'R)-lutein and (3R,3'R)-zeaxanthin was shown to not only result in an increase in the blood levels of these compounds in humans but also increased the concentration of their oxidative metabolites in plasma (Khachik et al., *J. Cellular Biochem.* 22:236–246 (1995)). These findings, for the first time, provided preliminary evidence for the long standing hypothesis that carotenoids may function as antioxidants in disease prevention. In addition, these results also established the importance of non-vitamin A active dietary carotenoids, particularly, lutein, zeaxanthin, and lycopene.

In 1985 and 1993, Bone et al., *Vision Res.* 25:1531–1535 (1985); *Invest. Ophthalmol. Vis. Sci.* 34:2033–2040 (1993), elegantly demonstrated that the human macular pigment is a combination of lutein and zeaxanthin and speculated that these dietary carotenoids may play an important role in the prevention of an eye disease, namely, Age-Related Macular Degeneration (ARMD). This was later confirmed in a case-controlled epidemiological study in which the high consumption of fruits and vegetables, rich specifically in lutein and zeaxanthin, was correlated to a 43% lower risk of ARMD (Seddon et al., *J. Am. Med. Assoc.* 272:1413–1420 (1994). More recently, in addition to lutein and zeaxanthin, the isolation and identification of one major and several minor oxidation products of lutein and zeaxanthin in human and monkey retinas was reported (Khachik et al., *J. Invest. Ophthalmol. Vis. Sci.* 38:1802–1811 (1997)). Metabolic pathways for these compounds were proposed which may play an important role in the prevention of ARMD. Therefore the commercial production of the purified forms of dietary carotenoids in general, particularly lutein and zeaxanthin, is of great importance. These carotenoids may be used, individually or in combination, as nutritional supplements and food colorants as well as in clinical trials where their potential health benefits in the prevention of ARMD and cancer can be investigated.

Although lutein and zeaxanthin may be obtained from certain fruits and vegetables, the isolation of lutein from extracts of marigold flowers and zeaxanthin from berries of Lycium Chinese Mill (LCM berries) proves to be most economical. In Marigold flowers, lutein is the major carotenoid and is normally accompanied by about 3–6% zeaxanthin; in LCM berries zeaxanthin is the major carotenoid and is completely free from lutein. In both of these plants, lutein and zeaxanthin are esterified with fatty acids such as lauric, myristic, and palmitic acids. However, dietary carotenol fatty acid esters, in general, have not been detected in human plasma or serum. Therefore, upon ingestion of purified lutein fatty acid esters by humans, these compounds partially undergo hydrolysis in the presence of pancreatic secretions in the small intestine to regenerate free lutein which is then absorbed (Khachik et al., *Pure & Appl. Chem.* 63 (1):71–80 (1991)).

A method for the purification of free lutein from extracts of marigolds was first reported in 1991 (Tyzkowski and Hamilton, *Poultry Sci.* 70(3):651–654 (1991)). However because this method was extremely time-consuming, used harmful organic solvents, and produced poor yields, it was not implemented commercially.

U.S. Pat. No. 4,048,203 describes a method for the purification of lutein fatty acid esters from marigold flowers. This method disclosed the use of hot (75° C.) isopropanol in purifying the lutein esters by recrystallization.

U.S. Pat. No. 5,382,714 describes a process for isolation, purification, and recrystallization of lutein from saponified Marigold oleoresin. The saponified Marigold oleoresin was obtained from Kemin Industries (Des Moines, Iowa) and is normally prepared by extraction of dried Marigold petals with n-hexane, followed by saponification and solvent evaporation.

This process for isolating lutein and zeaxanthin generally has at least one major disadvantage. At the last purification step, this process employs dichloromethane and n-hexane as the recrystallization solvents to obtain lutein containing 3–6% zeaxanthin in purities of 97% or greater. Since, according to the FDA, the use of dichloromethane and hexane in drug and food products should be limited, the lutein purified by these solvents should be thoroughly dried under high vacuum to remove residual solvents.

U.S. Pat. No. 5,648,564 describes a process for the isolation of lutein from a saponified Marigold oleoresin wherein lutein can be obtained in 70–85% purity. This process employs propylene glycol (40.9% weight percent) and an aqueous alkali (18.2% weight percent) to saponify a hexane extract of dried Marigold petals (marigold oleoresin, 40.9% weight percent) containing lutein esters at 70° C. in 10 hours.

There are several major disadvantages with this process. The Marigold oleoresin is prepared by extraction of dried marigold petals in boiling n-hexane for extended periods of time. In the next step of this process, the hydrolysis of lutein and zeaxanthin esters in the marigold oleoresin is conducted in an aqueous solution in the presence of alcohol and propylene glycol in which the fatty acid esters of lutein and zeaxanthin have very low solubility. As a result, this process requires high temperatures of up to 70° C. and 10 hours to complete the saponification. Due to the high viscosity of propylene glycol, during handling and several purification steps, the saponified product is additionally subjected to high temperatures ranging from 70 to 85° C.

U.S. Pat. No. 6,191,293 describes a method for isolating lutein and zeaxanthin esters from marigold flowers and Chinese Wolfberries. Hexane is used as a solvent for extraction at room temperature, but temperatures of 60° C. are used to evaporate the hexane. An additional step is required in which the isolated oleoresin is mixed with an alcohol to remove some of the by-product impurities. Separation and drying of the insoluble solids gave the final product. The carotenoid esters thus obtained contained 10% of the isomerized diester by-product.

U.S. Pat. No. 6,262,284 describes a method of isolating lutein and zeaxanthin by simultaneous extraction and saponification at room temperature using tetrahydrofuran and alcoholic potassium or sodium hydroxide. Upon neutralization and evaporation of the solvents, the free acid crystallized. The acids were recrystallized for purification.

The present invention is directed to a convenient and economical route for the isolation of lutein, zeaxanthin, and several minor carotenoids and the corresponding diesters. The methods employ either a simultaneous extraction and saponification procedure at room temperature for only a few hours or a two-step extraction saponification process also at room temperature. Most importantly, this process addresses all the disadvantages and concerns with regard to all of the previously described procedures. As a result, the lutein and zeaxanthin diesters obtained by this procedure contain substantially no isomerized by-products. In addition, the lutein (from Marigolds) and zeaxanthin (from LCM berries) obtained by this process are in purity of 97% or greater and are therefore suitable for human consumption.

BRIEF SUMMARY OF THE INVENTION

In one embodiment, the present invention relates to the extraction of carotenoid esters, with substantially no isomerization of the double bonds, from a plant source containing carotenoid esters, comprising extracting carotenoid esters from said plant source by contacting the plant source with one or more solvents to obtain a mixture; removing undissolved solids to obtain a liquids portion; removing the one or more solvents from the mixture under conditions which result in substantially no double bond isomerization to obtain a residue; and isolating the carotenoid esters.

In an alternative embodiment, the present invention relates to saponifying carotenoid esters, with substantially no isomerization of the double bonds, comprising contacting said esters with a solution comprising tetrahydrofuran and an alcohol at an elevated pH to obtain a mixture comprising hydrolyzed carotenoid; neutralizing the base with a dilute acid; removing the tetrahydrofuran and alcohol under conditions which result in substantially no double bond isomerization to obtain a residue comprising carotenoids free from esters; washing the residue with an aqueous solution to give carotenoid crystals; and collecting the carotenoid crystals.

In an alternative embodiment, the invention relates to the simultaneous extraction and hydrolysis of lutein esters or zeaxanthin esters, with substantially no isomerization of the double bonds, from at least one of marigold petals and Chinese Wolfberries, comprising extracting and saponifying said lutein esters and/or zeaxanthin esters from said petals or said berries by contacting said petals and/or said berries with a solution comprising tetrahydrofuran and an alcohol at an elevated pH to obtain a mixture comprising hydrolyzed lutein or zeaxanthin; removing solids from the mixture to obtain a liquids portion; stirring at room temperature; neutralizing the solution with a dilute acid; removing the tetrahydrofuran and alcohol from the liquids portion under conditions which result in substantially no double bond isomerization to obtain a residue comprising lutein free from esters and/or zeaxanthin free from esters; washing the residue with an aqueous mixture to give lutein and/or zeaxanthin crystals; and collecting lutein and/or zeaxanthin crystals.

In an alternative embodiment the present invention relates to the extraction of zeaxanthin esters with substantially no isomerization of the double bonds from Chinese Wolfberries containing zeaxanthin esters, comprising contacting the Chinese Wolfberries with one or more solvents to obtain a mixture; removing undissolved solids to obtain a solution of the zeaxanthin esters; adding water to the solution; removing the one or more solvents from the solution under conditions which result in substantially no double bond isomerization; adding one or more solvents to the residue; and isolating zeaxanthin esters.

In an alternative embodiment the present invention relates to saponifying zeaxanthin esters, with substantially no isomerization of the double bonds, comprising contacting said esters with a solution comprising tetrahydrofuran and methanol or ethanol at pH about 12 to obtain a mixture comprising hydrolyzed zeaxanthin; contacting the mixture with an acid such that the pH of the mixture is about 7.0–7.5; removing the tetrahydrofuran and methanol or ethanol under conditions which result in substantially no double bond isomerization, to obtain a residue comprising zeaxanthin free from esters; contacting the residue with a solvent to give zeaxanthin crystals; and collecting the zeaxanthin crystals.

The processes described above are convenient and commercially viable methods for extraction and isolation of carotenoid esters or carotenoids from plant sources in which these compounds are esterified with fatty acids. The production of carotenoid esters or carotenoids according to this process is preferably conducted under controlled and mild conditions at room temperature or below 40° C. to avoid the isomerization and degradation of these heat-sensitive compounds. Consequently, the carotenoid esters or carotenoids produced according to these procedures can be safely used as nutritional supplements or food coloring additives.

DETAILED DESCRIPTION OF THE INVENTION

Nomenclature

For convenience, the trivial rather than the correct systematic names of carotenoids have been used throughout this text. The chemical structures of lutein ((3R,3'R,6'R)-lutein), zeaxanthin ((3R,3'R)-zeaxanthin), alpha-cryptoxanthin ((3R,6'R)-alpha-cryptoxanthin), and beta-cryptoxanthin (3R-beta-cryptoxanthin), isolated from Marigold flowers (*Tagete erecta*) and berries of Lycium Chinese Mill, have been established to be identical with the dietary forms of these compounds found in most fruits and vegetables. The terms all-E and Z isomers of carotenoids refer to all-trans and cis isomers of these compounds. For in-chain geometrical isomers of carotenoids, the terms all-trans and cis, which have been used with the old nomenclature, are no longer appropriate. If not specified, the terms lutein or zeaxanthin refer to the most common geometrical forms (all-E or all-trans) of these carotenoids in plants. The use of the term "lutein esters" or "zeaxanthin esters" refers to either mono- or diesters without limitation.

In one embodiment, the present invention applies a simultaneous extraction and saponification process to two generally different plant sources for isolation of lutein and zeaxanthin; these are: dried petals of Marigolds (*Tagete erecta*) and LCM berries (Lycium Chinese Mill). These plant sources of carotenoids are described as follows.

The dried petals of marigold flowers, are harvested and prepared in Central America and are imported into the U.S. Flowers are hand-picked and ensiled to preserve them until they can be economically dried. The marigold blossoms are then placed in a freeze drying apparatus and are dehydrated under controlled conditions. After dehydration, the flowers are put through a series of air separators and mechanical separators where the petals are separated from any other materials and converted to a homogenous Marigold meal. The carotenoids in Marigold meal are esterified with fatty acids such as lauric, myristic, and palmitic acid, however, upon hydrolysis the parent hydroxycarotenoids are regenerated. As shown in U.S. Pat. No. 5,382,714, the major hydroxycarotenoid in Marigold is lutein which is normally accompanied by 3–6% of its isomeric compound, zeaxanthin.

LCM berries are normally grown in China and can be obtained from most of the Chinese supermarkets across the U.S. However, a variety of this fruit is also currently grown on a commercial scale by Rehnborg Center for Nutrition in Lakeview, Calif. For the first time in 1995, several grams of zeaxanthin was isolated from LCM berries for a human supplementation study and it was demonstrated that this plant is an excellent source of zeaxanthin (Khachik et al., *J. Cellular Biochem.*, 22:236–246 (1995)). However, the details of the isolation and purification of zeaxanthin were not published. Zeaxanthin in LCM berries is mostly esterified with palmitic acid and only trace amounts of this compound is esterified with lauric and myristic acids. LCM berries do not contain any measurable amount of lutein but several other carotenoids such as alpha-cryptoxanthin, beta-cryptoxanthin, and beta-carotene are present in this fruit in minute quantities. For the present study, large quantities of the berries were purchased from a local Chinese supermarket.

In one embodiment of the present invention, the choice of tetrahydrofuran (THF) as the extracting solvent was based on a guideline set by the Department of Health and Human Services, Food and Drug Administration (FDA) in Docket No. 97D-0148 published in Federal Register: May 2, 1997 (volume 62, Number 85, pages 24301–24309). The draft guideline entitled "Impurities: Residual Solvents" and was prepared under the auspices of the International Conference on Harmonization (ICH) of Technical Requirements for Registration of Pharmaceuticals for Human Use. The draft guideline recommends acceptable amounts of residual solvents in pharmaceuticals for the safety of the patient as well as recommending the use of less toxic solvents in the manufacture of drug substances and dosage forms. According to these guidelines, solvents are divided into three classes. These are:

Class 1: Solvents to be avoided. Known human carcinogens, strongly suspected human carcinogens, and environmental hazards.

Class 2: Solvents to be limited. Nongenotoxic animal carcinogens or possible causative agents of other irreversible toxicity such as neurotoxicity or teratogenicity; solvents suspected of other significant but reversible toxicities.

Class 3: Solvents with low toxic potential to man. No health based exposure limit is needed. Class 3 solvents have Permitted Daily Exposure (PDE) of 50 milligrams (mg) or more per day.

Ethanol and THF employed in one embodiment of the present invention are listed by the FDA in Class 3 and are therefore quite safe for commercial production of carotenoids for human use. The advantage of THF in comparison to other organic solvents of Class 3 is that carotenoids of the present invention are highly soluble in this solvent, which allows the extraction of these pigments from the matrices of various plants in an efficient manner. In addition, THF is water soluble and therefore can be used in a homogenous phase extraction of carotenoids from plants in which significant amounts of water may be present. The solubility strength of THF for carotenoids and the homogeneity of THF, ethanol, and water allow for the simultaneous extraction and saponification of carotenoids from plants. This is because the extracted carotenoids in a homogenous phase can be readily hydrolyzed at room temperature within several hours whereas in a heterogenous phase immiscible solvents such as a mixture of hexane, an alcohol, and water, would require high temperatures over extended period to accomplish the hydrolysis. The heterogeneous phase hydrolysis of carotenoids can present a serious problem especially in scaling up for commercial production. In such cases, the unavoidable high temperatures used for hydrolysis can increase the risk of oxidative degradation and isomerization of carotenoids.

In an exemplary process for this embodiment, Marigold meal (100 g), tetrahydrofuran (THF, 1000 ml), and sodium- or potassium hydroxide (25 g) in food grade methanol (250 nm) are homogenized at room temperature. The homogenate is steeped at an elevated pH of about 11–14, preferably about 12, for about two hours. Alternative alcohols for use in the present invention include 1-butanol, 2-butanol, 2-methyl-1-propanol, 1-propanol, and 2-propanol, which are all listed as safe in Class 3 solvents by the FDA. Preferred solvents are also selected for their boiling points. Solvents with boiling points of about 75° C. to 120° C. are preferred. Ethanol, with a boiling point of 78° C., is most preferred. The pH of the mixture is monitored and automatically maintained at about pH 12. An additional amount of sodium- or potassium hydroxide (25 g) in 250 ml of ethanol is normally needed to maintain the pH at 12. The extraction and saponification is completed in about 2 hours. The mixture is filtered and the filtrate is stirred at room temperature for 1 hour and the solution is treated with a dilute acid until the pH is 7.0–7.4. The solvents are then evaporated and the residue is washed with 1000 ml of a 1/1 mixture water and alcohol to remove the base and the water soluble components. The lutein crystals are collected by centrifugation, washed with alcohol (100 ml), and dried under high vacuum overnight at room temperature. The lutein crystals (2.0 g) obtained are about 75% pure and can be recrystallized from a mixture of THF (20 ml) and water (30 ml) and dried under high vacuum overnight to give 1.2 g of lutein containing about 5% zeaxanthin in 97% purity.

In an alternative embodiment of this invention, zeaxanthin diesters can be isolated in pure form with substantially no isomerized by-products. The choice of extracting solvent is based on the boiling point of the solvent and the cost associated with its use. Preferred solvents have low boiling points of around 50–120° C. so that none of the processes, including extraction, isolation and purification, will require elevated temperatures. While not wanting to limit the scope of the present invention by any single theory, it is believed that high temperatures cause isomerization of the biologically active, all-trans carotenoids. This leads to formation of isomerized by-products and limits the overall usefulness of the extracted carotenoid. Also, high temperatures may cause the carotenoid esters to become oxidized, thus eliminating the biological activity. Therefore, temperatures of the processes for this embodiment are below around 40–50° C. and more preferably below 40° C. Preferred solvents also have low costs associated with their use. Preferred solvents of the embodiment include, but are not limited to, hexanes, cyclohexane, petroleum ethers and THF.

In an exemplary process of this embodiment, powdered Chinese Wolfberries (20 g) and hexane or petroleum ether (100 mL) are stirred at room temperature for about 3 hours. Upon filtering the solution and washing the berries with hexane (50 mL) a clear dark yellow solution is obtained. The mixture is filtered and the filtrate is stirred at room temperature for 1 hour and the solution is treated with a dilute acid until the pH is 7.0–7.4. After adding water (5 mL) and distilling off the hexane or petroleum ether under reduced pressure, at or near room temperature, the product crystallizes out of solution. The purified product is collected by filtration or centrifugation and is washed with acetone (1 mL) and dried.

When the extraction solvents are evaporated at or below 50° C., substantially no isomerized by-products are obtained. By the term "substantially no isomerized by-products," it is intended that more than 90%, preferably 95% or more, most preferably, about 96% of the lutein or zeaxanthin diesters are in the trans configuration.

The levels of isomerized by-products in the isolated carotenoid esters are determined according to Khachik, et al, *J. Chromatogr,* 449:119–133 (1988).

The following examples are illustrative, but not limiting, of the methods and compositions of the present invention. Other suitable modifications and adaptations of the variety of conditions and normally encountered in natural products isolation techniques, which are obvious to those skilled in the art are within the spirit and scope of the present invention.

EXAMPLE 1

Isolation of Lutein from Marigold Mill by Simultaneous Extraction and Saponification Marigold mill (100 g) was vigorously homogenized in a blender with tetrahydrofuran (THF, 1000 ml) and 10% methanolic potassium hydroxide (KOH 150 ml) at room temperature for 2 hours. The mixture was filtered and the solid was washed with 200 ml of THF and the combined dark red solution was stirred at room temperature for one hour. The solution was then treated with a 2.5 N solution of hydrochloric acid (prepared from 25 ml of concentrated hydrochloric acid (36.5–38.0%) and 75 ml of water) until the pH dropped to 7.4. Once the pH was lowered to 12, the acid was added very slowly because there was a sudden drop in pH from 12 to 7.4 with the addition of only a small amount of acid. Therefore, the addition of the acid was carefully monitored by a pH meter and enough acid was added to bring the pH to 7.0–7.5. The pH should not be below 7. Water (15 ml) was added and THF (b.p. 65–67° C. at atmospheric pressure) and methanol (b.p. 64.7° C. at atmospheric pressure) were evaporated under reduced pressure between 40–50° C. (bath temperature) until the remaining solvent was mostly water. The evaporation of the solvents was carried out under reduced pressure and the temperature of the solution did not exceed 50° C. because lutein may undergo isomerization at elevated temperatures. Lutein crystallized as a dark yellow solid suspended in mostly water. The solution was allowed to cool down to room temperature and was treated with ethanol (15 ml). The mixture was stirred at room temperature or between 5–10° C. for 10 minutes to solubilize all the water-soluble particles. The suspension was filtered or centrifuged and the collected lutein crystals were washed with 20 ml of cold (5–10° C.) ethanol and dried under high vacuum at 60° C. overnight. The isolated yield of lutein was 2.0 g (75% pure).

EXAMPLE 2

Isolation of Zeaxanthin from Chinese Wolfberries by Simultaneous Extraction and Saponification 20 g of dried LCM berries were pulverized in a coffee bean mill and placed in a reactor and treated with tetrahydrofuran (THF, 60 ml) and 40 ml of methanolic KOH (5%). The mixture was stirred at room temperature for 10 hours. To shorten the extraction time from 10 to 2 hours, berries with smaller particle size were used and the mixture heated at 50° C. The mixture was allowed to cool down to room temperature and was filtered through celite. The powdered berries were washed with 50 ml of methanol and the combined clear dark yellow solution were stirred at room temperature for one hour. The pH of the solution was measured at 13.7. The solution was treated with 5.9 ml of 2.5 N solution of hydrochloric acid (prepared from 25 ml of concentrated hydrochloric acid (36.5–38.0%) and 75 ml of water). After the addition of acid, the pH dropped to 7.4. The acid was added very slowly because there was a sudden drop in pH from 12 to 7.4 with the addition of only a small amount of acid. Therefore, the addition of the acid was carefully monitored by a pH meter and enough acid was added to bring the pH to 7.0–7.5. The pH did not go below 7. THF (b.p.=65–67° C. at atmospheric pressure) and methanol (b.p.=64.7° C. at atmospheric pressure) were evaporated under reduced pressure between 40–50° C. (bath temperature) until a few mls of solvent (mostly water) remained. The evaporation of the solvents was carried out under reduced pressure and the temperature of the solution did not exceed 50° C. because zeaxanthin may undergo isomerization at elevated temperatures. Zeaxanthin crystallized as a dark yellow solid suspended in water. The solution was cooled to room temperature and was treated with water (3 ml) and ethanol (4 ml). The crystals were stirred at room temperature or between 5–10° C. for 10 minutes. The suspension was filtered or centrifuged and the collected zeaxanthin crystals were washed with 41 ml of cold (5–10° C.) ethanol and dried under high vacuum at 60° C. overnight. The isolated yield of zeaxanthin was 16.4 mg (80% pure). The yield of the 80% purified zeaxanthin was 0.082 g/100 g of LCM berries extracted.

EXAMPLE 3

Isolation of Zeaxanthin Dipalmitate (Physalien) from Chinese Wolfberries Employing Tetrahydrofuran (THF) as Solvent 20 g of dried LCM berries were pulverized in a coffee bean mill and placed in a reactor and treated with tetrahydrofuran (THF, 70 ml). The mixture was stirred at room temperature for 6 hours. To shorten the extraction time, berries with smaller particle size were used and the mixture was heated at 50° C. for 1 h. The solution was filtered through celite. The powdered berries were washed with 30 ml of THF to obtain a clear dark yellow solution. Water (5 ml) was added and THF (b.p.=65–67° C. at atmospheric pressure) was evaporated under reduced pressure between 40–50° C. (bath temperature) until the remaining solvent was mostly water. The evaporation of the solvents was carried out under reduced pressure and the temperature of the solution did not exceed 50° C. Zeaxanthin dipalmitate crystallized as a dark red solid suspended in mostly water. The solution was allowed to cool down to room temperature and was then treated with acetone (3 ml). This was stirred at room temperature for 10 minutes to solubilize all the water-soluble particles. The suspension was filtered or centrifuged and the collected zeaxanthin dipalmitate crystals were washed with 3 ml of acetone and dried under high vacuum at 60° C. overnight. The isolated yield of zeaxanthin dipalmitate was 36.0 mg (80% pure).

EXAMPLE 4

Isolation of Zeaxanthin Dipalmitate (Physalien) from Chinese Wolfberries Employing Hexanes or Petroleum Ether (b.p.=35–66° C.)

20 g of dried LCM berries were pulverized in a coffee bean mill into a powder. The powder was placed in a container and treated with 100 ml of hexanes or 100 ml of petroleum ether (b.p.=35–60° C.). The mixture was stirred vigorously at room temperature for 3 hours. The extraction time can be shortened to 1 hour if the extraction is carried out at 50° C. After 3 h, the solution was filtered through celite. The powdered berries were washed with 50 ml of hexanes or petroleum ether to obtain a clear dark yellow solution. Water (5 ml) was added and hexanes (b.p.=68–70° C. at atmospheric pressure) or petroleum ether (b.p.=35–66° C.) was distilled under reduced pressure between 40–50° C. (bath temperature) until the remaining solvent was mostly water. The evaporation of 4 hexanes or petroleum ether was carried out under reduced pressure and the temperature of the solution did not exceed 50° C. because zeaxanthin dipalmitate undergoes isomerization at elevated temperatures. At this point, zeaxanthin dipalmitate crystallized as a dark red solid. The solids were treated with 1 ml of acetone and the suspension was centrifuged (or filtered) to give zeaxanthin dipalmitate (32 mg, 80% pure). The crystalline product was vacuum dried at 60° C.

EXAMPLE 5

Extraction of Zeaxanthin Dipalmitate from Chinese Wolfberries Employing Cyclohexane Dried LCM berries (20 g) were pulverized in a coffee bean mill into a powder. The powder was placed in a three-necked flask equipped with a magnetic bar, a thermometer, and a condenser. Cyclohexane (100 ml) was added and the flask was immersed in a pre-heated oil bath maintained at approximately 55° C. The oil-bath temperature was adjusted so that the temperature of the solution remained between 47–50° C. The mixture was stirred magnetically at this temperature for 1 hour. Heating was discontinued and the solution was allowed to cool down to room temperature. The mixture was filtered through celite and the powdered berries were washed with 50 ml of cyclohexane and gave a clear dark yellow solution. Water (5 ml) was added and cyclohexane (b.p.=80.7° C. at atmospheric pressure) was distilled under reduced pressure between 40–50° C. (bath temperature) until most of the solvent was evaporated and the residue is mostly water. The evaporation of cyclohexane was carried out under reduced pressure and the temperature of the solution did not exceed 50° C. Zeaxanthin dipalmitate crystallized as a dark red solid. The residue was treated with 1 ml of acetone and the suspension was centrifuged (or filtered) to give 36 mg of trans-zeaxanthin dipalmitate (96%), 9-cis-zeaxanthin dipalmitate (3%), and 13-cis-zeaxanthin dipalmitate (1%). The crystalline, product was dried under vacuum at 60° C.

EXAMPLE 6

Isolation of Zeaxanthin by Saponification of Zeaxanthin Dipalmitate Extracted from Chinese Wolfberries Zeaxanthin dipalmitate (36 mg) was dissolved in 3 ml of tetrahydrofuran (THF) and was treated with 1 ml of 10% KOH in methanol or ethanol. The mixture was stirred at room temperature for 1 hour to complete the hydrolysis of zeaxanthin dipalmitate to zeaxanthin. The pH of the solution was measured at 12. The solution was treated with 0.5 ml of 2.5 N solution of hydrochloric acid prepared from 2.5 ml of concentrated hydrochloric acid and 7.5 ml of water. After the addition of acid, the pH dropped to 7.4. Once the pH was lowered to 12, the acid was added very slowly because there was a sudden drop in pH from 12 to 7.4 with the addition of only a small amount of acid. Therefore, the addition of the acid was carefully monitored by a pH meter and enough acid was added to bring the pH as close as possible to pH=7.0–7.5. The pH did not go below 7. The, THF (b.p.=65–67° C. at atmospheric pressure) and methanol (b.p.=64.7° C. at atmospheric pressure) are co-distilled under reduced pressure between 40–50° C. (bath temperature) until a few ml of solvents remained. The evaporation of the solvents was carried out under reduced pressure and the temperature of the solution did not exceed 50° C. because zeaxanthin may undergo isomerization at elevated temperatures. 1 ml of hexanes was added and zeaxanthin crystallized as a dark yellow-orange solid. The crystals were centrifuged and vacuum dried at 60° C. The yield of zeaxanthin was 16 mg.

From the above examples it can be seen that the present invention has accomplished the isolation of lutein and zeaxanthin esters with substantially no isomerized by-products. This economically viable process employs solvents which are not toxic and as a result, the carotenoid purified by this procedure can be safely used as nutritional supplements or food coloring additives. All publications, patents and patent applications cited herein are fully incorporated by reference.

What is claimed is:

1. A method for the extraction of carotenoid esters, with substantially no isomerization of the double bonds, from a plant source containing carotenoid esters, comprising extracting carotenoid esters from said plant source by contacting the plant source with one or more solvents to obtain a mixture; removing undissolved solids to obtain a liquids portion; removing the one or more solvents from the mixture under conditions which result in substantially no double bond isomerization to obtain a residue; and isolating the carotenoid esters; wherein said one or more solvents comprises tetrahydrofuran.

2. The method of claim 1 wherein said carotenoid esters comprise lutein esters or zeaxanthin esters.

3. The method of claim 1 wherein said carotenoid esters comprise at least 95% all trans zeaxanthin esters.

4. The method of claim 1 wherein said conditions comprise evaporating said solvents at or below 50° C.

5. The method of claim 1 wherein said conditions further comprise evaporating the solvents under reduced pressure.

6. The method of claim 1 wherein the plant source is Lycium Chinese berries or marigold petals.

7. A method for the extraction of carotenoid esters, with substantially no isomerization of the double bonds, from a plant source containing carotenoid esters, comprising extracting carotenoid esters from said plant source by contacting the plant source with one or more solvents to obtain a mixture; removing undissolved solids to obtain a liquids portion; removing the one or more solvents from the mixture under conditions which result in substantially no double bond isomerization to obtain a residue; isolating the carotenoid esters, and saponifying said carotenoid esters with a solution comprising tetrahydrofuran and an alcohol at an elevated pH to obtain a mixture comprising hydrolyzed carotenoid; neutralizing the base with a dilute acid; removing the tetrahydrofuran and alcohol under conditions which result in substantially no double bond isomerization to obtain a residue comprising carotenoids free of esters; washing the residue with an aqueous solution to give carotenoid crystals; and collecting the carotenoid crystals.

8. The method of claim 7 wherein said carotenoids comprise lutein or zeaxanthin.

9. The method of claim 7 wherein said conditions comprise evaporating said solvents at or below 50° C.

10. The method of claim 9 wherein said conditions further comprise evaporating said solvents under reduced pressure.

11. A method for saponifying carotenoid esters, with substantially no isomerization of the double bonds, comprising contacting said esters with a solution comprising tetrahydrofuran and an alcohol at an elevated pH to obtain a mixture comprising hydrolyzed carotenoid; neutralizing the base with a dilute acid; removing the tetrahydrofuran and alcohol under conditions which result in substantially no double bond isomerization to obtain a residue comprising carotenoids free from esters; washing the residue with an aqueous solution to give carotenoid crystals; and collecting the carotenoid crystals.

12. The method of claim 11 wherein said carotenoids comprise lutein or zeaxanthin.

13. The method of claim 11 wherein said conditions comprise evaporating said solvents at or below 50° C.

14. The method of claim 13 wherein said conditions further comprise evaporating the solvents under reduced pressure.

15. The method of claim 11 wherein the alcohol is selected from the group consisting of methanol, ethanol, 1-butanol, 2-butanol, 2-methyl-1-propanol, 1-propanol, and 2-propanol.

16. The method of claim 11 wherein said saponifying further comprises monitoring the pH; and adjusting the pH by adding base.

17. The method of claim 16 wherein said base is NaOH or KOH.

18. The method of claim 11 wherein the pH is about 12.

19. A method for the simultaneous extraction and hydrolysis of lutein esters or zeaxanthin esters, with substantially no isomerization of the double bonds, from at least one of marigold petals and Chinese Wolfberries, comprising extracting and saponifying said lutein esters and/or zeaxanthin esters from said petals or said berries by contacting said petals and/or said berries with a solution comprising tetrahydrofuran and an alcohol at an elevated pH to obtain a mixture comprising hydrolyzed lutein or zeaxanthin; removing solids from the mixture to obtain a liquids portion; stirring at room temperature; neutralizing the solution with a dilute acid; removing the tetrahydrofuran and alcohol from the liquids portion under conditions which result in substantially no double bond isomerization to obtain a residue comprising lutein free from esters and/or zeaxanthin free from esters; washing the residue with an aqueous mixture to give lutein and/or zeaxanthin crystals; and collecting lutein and/or zeaxanthin crystals.

20. The method of claim 19 wherein the alcohol is selected from the group consisting of ethanol, 1-butanol, 2-butanol, 2-methyl-1-propanol, 1-propanol, and 2-propanol.

21. The method of claim 19 further comprising washing the collected lutein or zeaxanthin crystals with an alcohol having a boiling point between 75° C. and 120° C., and drying the crystals.

22. The method of claim 19 further comprising recrystallizing the lutein or zeaxanthin crystals from an aqueous mixture of tetrahydrofuran.

23. The method of claim 19 wherein said simultaneous extracting and saponifying further comprise monitoring the pH; and adjusting the pH by adding base.

24. The method of claim 19 wherein said base is NaOH or KOH.

25. The method of claim 19 wherein the marigold petals, prior to extraction, are milled to a meal.

26. The method of claim 19 wherein the pH is about 12.

27. A method for the extraction of zeaxanthin esters with substantially no isomerization of the double bonds from Chinese Wolfberries containing zeaxanthin esters, comprising contacting the Chinese Wolfberries with one or more solvents to obtain a mixture; removing undissolved solids to obtain a solution of the zeaxanthin esters; adding water to the solution; removing the one or more solvents from the solution under conditions which result in substantially no double bond isomerization; adding one or more solvents to the residue; and isolating zeaxanthin esters.

28. The method of claim 27 wherein said zeaxanthin esters comprise at least 95% all trans zeaxanthin esters.

29. The method of claim 27, wherein said one or more solvents are hexanes, cyclohexane, petroleum ethers, acetone, or tetrahydrofuran.

30. The method of claim 27, wherein said contacting further comprises contacting the Chinese Wolfberries with one or more solvents at or below 50° C.

31. The method of claim 27, wherein said removing further comprises filtering or centrifuging the mixture to remove said undissolved solids.

32. The method of claim 27, wherein said conditions comprise evaporating said solvents at or below 50° C.

33. The method of claim 32, wherein said conditions further comprise evaporating the solvents under reduced pressure.

34. A method for saponifying zeaxanthin esters, with substantially no isomerization of the double bonds, comprising contacting said esters with a solution comprising tetrahydrofuran and methanol or ethanol at pH about 12 to obtain a mixture comprising hydrolyzed zeaxanthin; contacting the mixture with an acid such that the pH of the mixture is about 7.0–7.5; removing the tetrahydrofuran and methanol or ethanol under conditions which result in substantially no double bond isomerization, to obtain a residue comprising zeaxanthin free from esters; contacting the residue with a solvent to give zeaxanthin crystals; and collecting the zeaxanthin crystals.

35. The method of claim 34 wherein said acid comprises hydrochloric acid.

36. The method of claim 34 wherein said conditions comprise evaporating said solvents at or below 50° C.

37. The method of claim 34 wherein said conditions further comprise evaporating said solvents under reduced pressure.

38. The method of claim 1, wherein at least about 95% of the isolated carotenoid esters are in the trans-configuration.

* * * * *